United States Patent [19]

Wallshein

[11] 4,117,596
[45] Oct. 3, 1978

[54] APPARATUS AND METHOD FOR MOUNTING ORTHODONTIC APPLIANCES TO TEETH

[76] Inventor: Melvin Wallshein, 8645 Bay Pkwy., Brooklyn, N.Y. 11214

[21] Appl. No.: 813,337

[22] Filed: Jul. 6, 1977

[51] Int. Cl.² ............................................. A61C 7/00
[52] U.S. Cl. .................................................. 32/14 R
[58] Field of Search ................... 32/14 R, 14 A, 14 B, 32/14 C, 14 D, 14 E

[56] References Cited

U.S. PATENT DOCUMENTS 3,082,531   3/1963   Jacobson ................................. 32/63
3,521,355   7/1970   Pearlman ............................ 32/14 A Primary Examiner—Robert Peshock
Attorney, Agent, or Firm—Flynn & Frishauf

[57] ABSTRACT

A method and apparatus for mounting orthodontic appliances, such as brackets, to teeth involves the use of a tape which has an adhesive on a surface thereof, and means for mounting the appliance to the tape such that the rear surface of the appliance which is to be secured to a tooth is exposed to the tooth. The tape preferably comprises means for angularly and/or vertically indicating the orientation of the appliance relative to the tape so that it may be mounted to a tooth with a predetermined orientation. The tape preferably has an adhesive which adheres to wet or damp surfaces so that it is not necessary to completely dry the complete surface of the tooth on which the tape is to be mounted.

35 Claims, 13 Drawing Figures

APPARATUS AND METHOD FOR MOUNTING ORTHODONTIC APPLIANCES TO TEETH

This invention relates to apparatus and a method for mounting orthodontic appliances to teeth, and more particularly, to such an apparatus and method which facilitates mounting of a bracket on a tooth in a predetermined orientation.

Heretofore, mounting of orthodontic brackets directly to teeth, for example by means of adhesives, has been a time consuming and difficult task. Since the brackets are very small, they are difficult to handle and to precisely align on the teeth in predetermined orientations. Moreover, the difficulty in installing brackets on teeth is compounded in that it is sometimes necessary to manually hold the bracket in position on the tooth while the adhesive sets.

The object of the present invention is to provide a method and apparatus for mounting appliances to teeth, for example metal or plastic brackets, using an adhesive, which method and apparatus obviates the need for the orthodontist to manually place the bracket in place while the adhesive is setting.

A further object of the invention is to provide an apparatus and method which enables brackets to be easily aligned on teeth in predetermined desired orientations.

SUMMARY OF THE INVENTION

In accordance with the present invention, apparatus for mounting an orthodontic appliance, such as a bracket, on a tooth comprises an adhesive member which is adapted to be temporarily adhered to a surface of a tooth; the adhesive member including means for mounting an orthodontic appliance thereon and for retaining the appliance in a given orientation relative to the adhesive member. The adhesive member is provided with means for measuring and indicating the orientation of the appliance relative to the adhesive member.

In accordance with a further aspect of the invention, a method for positioning and mounting an orthodontic appliance on a tooth, comprises removably mounting an orthodontic appliance on an adhesive member having the aforementioned measuring and indicating means thereon; adhering the adhesive member to a surface of a tooth, and adhering the appliance to said surface of the tooth; and then removing the adhesive member from the tooth and from the appliance after the adhesive securing the appliance to said tooth has set.

DETAILED DESCRIPTION

Figure 1:
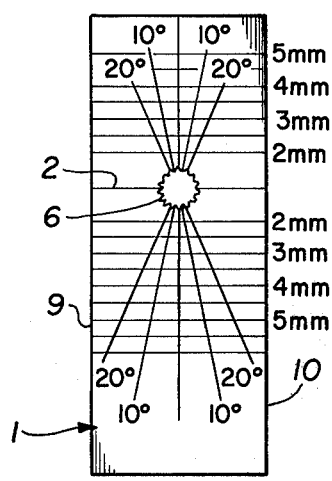
FIG. 1 is a front view of a typical tape-like device according to the present invention for mounting and orienting orthodontic brackets on teeth.

Referring to FIG. 1, a mounting device according to the present invention comprises a generally rectangular member 1 having an adhesive backing thereon. While the shape is shown in FIG. 1 as being generally rectangular, other shapes could be used, as desired. The rectangular member, hereinafter referred to merely as "tape", has index markings on the front surface thereof which are utilized by the operator in precisely and accurately mounting a bracket with a predetermined orientation on a tooth. The tape has angle markings, up to for example 0° ± 20° so that the bracket may be oriented at an angle on the face of a tooth. The tape also has horizontal index lines, for example up to 5 mm or more in both directions from a reference point 2 so that the bracket may be oriented on a tooth at a given predetermined distance from, for example, the biting edge of the tooth. The various angular markings on the front surface of the tape may be in different colors and/or in different thickness lines in order to facilitate use of the device.

Figure 2:
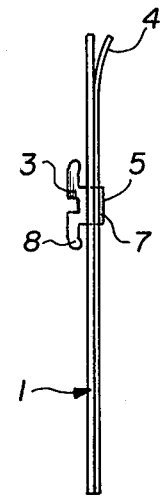
FIG. 2 is a side view of the device of FIG. 1 with a bracket held therein ready for mounting to a tooth.

FIG. 2 is a side view of the tape of FIG. 1 showing a bracket 3 mounted therein ready for mounting on a tooth. The tape 1, with the adhesive backing, preferably has a peel away backing 4 on the rear surface thereof to protect the adhesive during handling of the device. When ready for use, the backing 4 is peeled away, as shown in FIG. 2, and the device is adhesively mounted on a tooth with the appropriate adhesive on the rear surface 5 of the bracket 3 so that the bracket 3 may be adhered to the surface of the tooth.

It is preferred that the adhesive backing on the tape 1 be of a type which firmly adheres to even a wet or damp surface, and is easily peelable off of the wet or damp surface when desired. The adhesive used on the rear surface 5 of the bracket 3 may be conventional adhesives used, for example, to mount plastic or metal brackets to teeth. The tape is utilized to hold the bracket in position while the adhesive on the rear surface of the bracket 3 sets. After the adhesive on the rear surface of the bracket 3 sets, the tape 1 is peeled away from the tooth and bracket, leaving the bracket firmly and accurately mounted on the tooth. The tape preferably is longer at the lower end thereof, for example as shown in FIG. 1, so that it may be wrapped around the biting edge of the tooth and secured also to the rear surface of the tooth. This more securely retains the bracket in position during the period of time required for the adhesive on the rear surface of the bracket to set.

Tapes having the property of adhering to wet or damp surfaces are presently available. Examples of such tapes are the tapes included in 3M's surgical taping system, i.e., Micropore, Durapore, Transpor, and Blenderm (registered trademarks of the 3M Company), catalog numbers 1530, 1538, 1527 and 1525, respectively. Another tape is one using GP-25 adhesive on a backing, the adhesive being available from Coated Products, Middlesex, N.J.

As seen in FIG. 1, the tape 1 has an aperture 6 through which the bracket 3 is mounted. In a preferred embodiment, the opening 6 has serrated, jagged or cut edges so that the bracket 3 may be inserted into the opening with various angular orientations relative to the tape and be retained in the opening by means of the serrated or jagged edges of the opening 6. This is particularly advantageous when the invention is used to mount brackets 3 having generally rectangular base portions 7 which in turn may have a further base depending therefrom (not shown). The further base may be perforated, mesh, solid or have any other configuration to permit adhesion to the tooth. In this event, the corners of the base portion 7 engage the serrated or jagged edges of the opening 6, regardless of the orientation of the bracket relative to the tape.

The tape 1 preferably has elastic qualities in order to facilitate engagement with the bracket and removal of the tape from the bracket after the adhesion holding the bracket to the tooth is set. When the tape is pulled off of the tooth, the elastic quality facilitates removal of the tape from behind the wing portions 8 (FIG. 2) of the bracket.

In use, it is preferred that the tape 1 have substantially straight side edges 9 and 10. This will facilitate alignment of the tape 1 relative to the side edges of the tooth to insure that the tape 1 is always substantially parallel to the longitudinal axis of the tooth. The more closely aligned the tape is with the longitudinal axis of the tooth, the more accurate will be the angular alignment of the bracket when using the scale imprinted on the front surface of the tape 1. While the opening or aperture 6 in the tape 1 is shown as having jagged or serrated edges, this opening could have smooth edges, or could be generally oval as shown, for example in FIG. 3.

Figure 3:
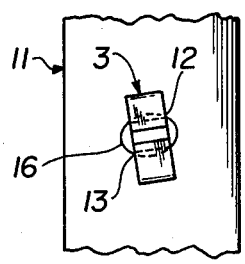
FIG. 3 illustrates a modification of the embodiment of FIGS. 1 and 2.

FIG. 3 partially illustrates a tape 11, similar to the tape 1 of FIG. 1, the scale markings being omitted for ease of illustration. The tape 11 has an opening 16 which is generally oval. A bracket 3 is shown mounted in the opening 16, the corners 12 and 13 of the base portion 7 of the bracket engaging side surfaces of the opening 16. Especially when the tape 11 is made of a material having elastic qualities, the bracket 3 is firmly retained in various angular positions, depending upon how it is inserted into the opening 16. Moreover, as the bracket 3 is moved to different positions along a horizontal line in FIG. 3, it is seen that the bracket will tend to take various angular orientations in the oval opening 6.

Instead of openings 6 or 16, the tape, if it is sufficiently resilient, may merely have a horizontal slit, for example, formed therein, through which the bracket is inserted for mounting on a tooth. Alternatively, both a horizontal and vertical slit may be provided, the slits crossing, for example, at the centers thereof.

Figure 4:
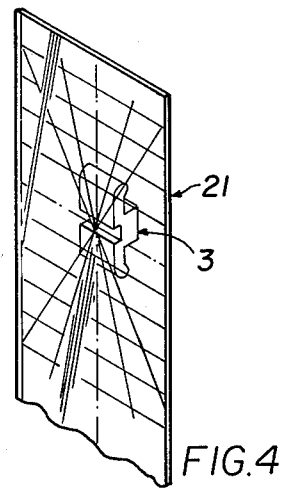
FIG. 4 illustrates a further embodiment of the invention.

FIG. 4 illustrates a modified embodiment of the invention which omits the opening 6 or 16 of the embodiments of FIGS. 1 and 3. The front surface of the bracket 3 is temporarily adhered to the rear adhesive surface of the tape 21 and the appropriate adhesive for mounting the bracket to a tooth is applied to the rear surface of the bracket 3. In the embodiment of FIG. 4, in order to facilitate orienting the bracket at predetermined angular positions and at predetermined vertical levels along the tape, the index markings may be imprinted on the rear surface of the tape so that they may be seen through a transparent or translucent adhesive surface on the rear of the tape 21, or the index markings may be imprinted on the front surface of the tape, the tape in this instance being transparent or translucent enough so that the bracket 3 can be seen through the tape.

Figure 5:
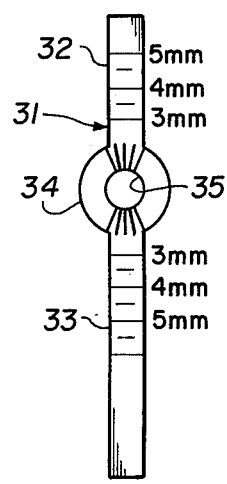
FIG. 5 illustrates a still further embodiment of the invention which is particularly useful for mounting brackets on anterior teeth.

FIG. 5 illustrates an embodiment which is particularly useful for mounting brackets on anterior teeth. The tape 31 includes thin portions 32,33 which are joined together by a bulged out portion 34. The bulged out or enlarged portion 34 has an opening 35 therein for receiving a bracket. The tape 31 has the appropriate height and angular markings, similar to those of FIG. 1. The tape preferably has a backing, as shown in FIG. 2, and is operated similarly to the embodiments of FIGS. 1 and 2. The opening 35 may have smooth edges, as shown in FIG. 5, or may have serrated, jagged or cut edges as shown in FIG. 1. The opening may also take the form of an oval as shown in FIG. 3 or slits. The lower portion 33 of the tape 31 is sufficiently long so as to wrap around the biting surface of the tooth and to be secured to the inner vertical surface of the tooth.

Figure 6:
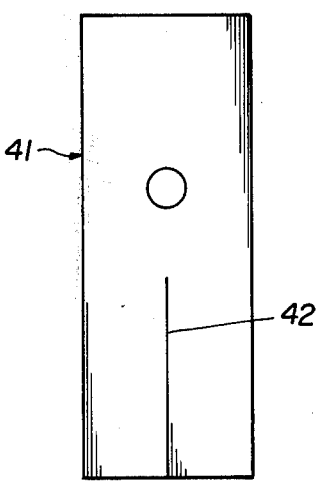
FIG. 6 illustrates another embodiment of the invention which is particularly useful for mounting of brackets on posterior teeth.

FIG. 6 illustrates an embodiment which is particularly useful for mounting of brackets on posterior teeth. The embodiment of FIG. 6 is similar to that of FIG. 1, the index markings being omitted for ease of illustration. The tape 41 of FIG. 6 has a vertical slit 42 in the lower portion thereof. The slit enables the tape to be wrapped around the lower pointed surfaces of, for example, posterior teeth so that the tape may more securely be held in position during setting of the adhesive on the rear of the bracket. Instead of the slit being permanently formed in the tape 41, the tape 1 of FIG. 1 may have a perforation in the position of the slit 42 so that the tape may be perforated to provide a slit similar to slit 42.

Figure 7:
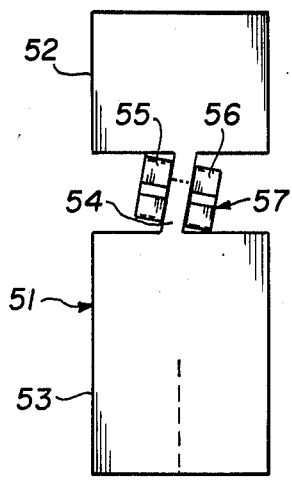
FIG. 7 illustrates a still further embodiment of the invention which mounts brackets to teeth with a fixed predetermined angular relationship.

FIG. 7 illustrates a still further embodiment of the present invention which is particularly useful in mounting twin brackets to teeth. The tape 51 comprises upper and lower portions 52,53 and an intermediate portion 54 connected therebetween. The intermediate portion 54 is substantially narrower than upper and lower portions 52 and 53 and is adapted to fit within the space between respective brackets 55,56 of a twin bracket 57 as shown in FIG. 7. In the embodiment of FIG. 7 the portion 54 is shown oriented at an angle of approximately 10° relative to the vertical. Thus, the embodiment of FIG. 7 will permit a twin bracket to be mounted to a tooth with a 10° angle to the vertical axis of the tooth in a simple and expedient manner. The lower portion 53 of the tape is adapted to wrap around the biting surface of the tooth.

In order that the tape 51 of FIG. 7 can be used to provide both left and right 10° angles, the tape preferably has adhesive on both opposing flat surfaces thereof and has respective backings on both opposing surfaces to protect the adhesive. In use, the tape will be oriented relative to the tooth so that only one backing is removed to mount the bracket, depending upon whether or not left or right 10° angles are desired. The embodiment of FIG. 7 is shown with a fixed angular relationship between the intermediate member 54 and the vertical axis. Additional tapes with different angular relationships of the intermediate member 54 may be provided to provide the orthodontist with a wide variety of possible angular relationships.

Figure 8:
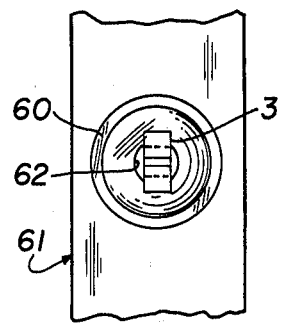
FIG. 8 illustrates an embodiment of the invention wherein the bracket is encapsulated or covered.

FIG. 8 illustrates another embodiment of the invention in which the bracket is encapsulated in, for example, a transparent capsule. Such a construction may be sold as one piece, ready to use in the mouth, or may be sold as components which are assembled by the orthodontist. This arrangement has the advantage that the bracket may be kept drier during the period of time required for setting of the adhesive to the tooth. The embodiment of FIG. 8 is used substantially the same as that of the previously described embodiments, and in particular FIG. 1. The capsule 60 is of transparent material and is secured, for example, to the outer surface of tape 61 by means of, for example, an adhesive. FIG. 8 illustrates a typical bracket 3 mounted in the tape 61 beneath the capsule 60. Since the tape 61 preferably has elastic qualities, the bracket 3 may be inserted through the opening 62 of the tape 61 by stretching the tape 61 at the opening 62. The bracket 3 may also be angularly oriented relative to the tape, as in FIG. 1.

Figure 9:
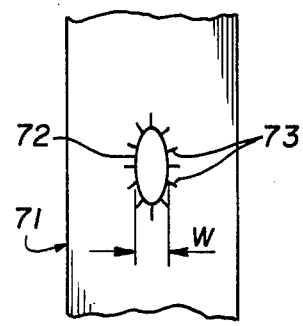
FIG. 9 illustrates yet another embodiment of the invention.

FIG. 9 illustrates an embodiment similar to that of FIG. 3, but with the oval opening 72 oriented in the vertical direction rather than the horizontal direction. Most brackets with which the device of the present invention is used have a uniform height and the base portion 7 (FIG. 1) has a generally uniform height. However, the widths of the brackets vary. For example, there are various width single brackets, and various width twin brackets. A twin bracket, for example, is shown in FIG. 7. If brackets of varying width are to be used with a tape of FIG. 3, there is a possibility that very narrow width brackets would be able to move in the horizontal direction in the oval opening 16 of the embodiment of FIG. 3. The embodiment of FIG. 9 is proposed to obviate this difficulty. In FIG. 9, the oval opening 72 has a maximum width "w" which is substantially the same as or just slightly smaller than the width of the narrowest bracket with which the present invention is to be used. Such a bracket may be inserted into the opening 72 in a normal manner, and may be angularly oriented as discussed with respect to FIGS. 1 and 3. When inserting a wide bracket, such as a twin bracket 57 of FIG. 7, the bracket is inserted with the width dimension in a vertical direction (that is, with the arch wire channel directed vertically or along the length of the oval opening 72) and the base portion of the bracket is inserted in the opening 72. Then, the bracket is twisted approximately 90°, thereby deforming the side walls of the opening 72 and increasing "w" of the opening 72. The tape is generally resilient enough to absorb the stretching resulting from turning of the bracket by 90° in the opening 72. In this manner, the tape 71 may accommodate brackets of varying width, while retaining all of the different width brackets in a relatively snug manner. The tape 71 of the embodiment of FIG. 9 also has index markings thereon, such as the markings of FIG. 1.

When the embodiment of FIG. 9 is provided with a capsule, such as capsule 60 of FIG. 8, the rigidity of the capsule prevents excessive deformation of the tape due to insertion of relatively wide brackets in the opening 72. This tends to keep the tape flatter and renders the tape 71 more easily used and aligned on a tooth.

As shown in FIG. 9, a plurality of slits 73 may be formed in the tape adjacent the opening 72. The slits 73 enable the tape to more firmly grip a bracket when it is oriented at given angles. The slits 73 may be spaced with predetermined spacings which correspond to predetermined angular increments on the tape. This will provide still easier alignment of the bracket in a predetermined direction. As discussed above, the tape of FIG. 9 preferably includes the angular and vertical height scales as shown in FIG. 1.

When the tapes of the present invention are mounted on teeth, the tapes may be long enough so as to extend onto the gum and adhere to the gum to provide still better retention of the tape in position during setting of the adhesive for the bracket.

Figure 10:
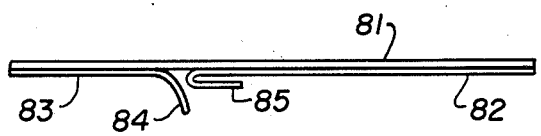
FIG. 10 shows a backing for the adhesive member which is easily removable.

FIG. 10 illustrates a tape 81 with a backing which is easily removable. The backing is comprised of first and second portions 82,83. The end portion 84 of the backing section 83 overlaps the first portion of the backing 82 and provides a tab for easy removal of the backing 83. The portion 82 may then be easily removed by gripping the free end 85 of the backing 82 to permit easy removal thereof. The overlap may be anywhere along the tape 81.

Figure 11:
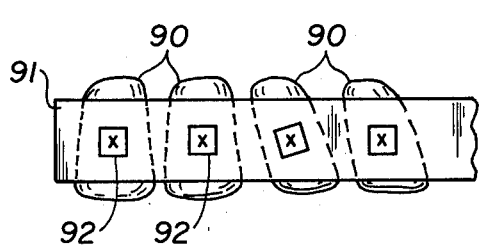
FIGS. 11 and 12 illustrate further embodiments of the invention.

FIG. 11 illustrates a plurality of teeth 90 on which a tape 91 according to the present invention is adhered. The tape is marked with small x points indicating the position at which a bracket, or the like, is to be secured to a tooth. The tape is then removed from the tooth and cut-outs 92 are formed in the tape, as shown in FIG. 11. The cut-outs may be oriented at various angular positions, depending upon the desired orientation of the bracket on the tooth. Then brackets are mounted on the tape in the openings 92 and are mounted to the teeth as described above with respect to, for example, FIG. 1. This arrangement is an advantageous way to mount a plurality of brackets in predetermined positions on adjacent teeth in an accurate and expedient manner.

Figure 12:
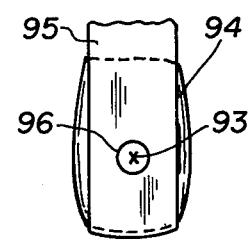

FIG. 12 illustrates a further embodiment of the invention which is used by, for example, marking an x or reference point 93 on a tooth 94 and then applying a tape 95 with an opening 96 therein. The opening 96 is centered around the marking point 93 so that the bracket, or the like, may be accurately secured to the face of the tooth 94. This arrangement enables the bracket to be accurately located at the marking point. In the event that the tape with the locating hole 96 is not used, it is possible that the bracket will not be properly mounted at the locating point since during mounting, the bracket obscures the locating point. In the embodiment of FIG. 12, the opening 96 is generally the same size as the portion of the bracket which will be adhered to the tooth and can be accurately located related to the marking point. During mounting of the bracket, the opening 96, if dimensioned so as to correspond to the size of the portion of the bracket adhered to the tooth, will support the bracket by friction against the side walls of the opening 96 during setting of the adhesive joining the bracket to the tooth.

The embodiment of FIG. 12 may be used in order to prepare a tooth, for example by etching, in an accurate manner. First a tape having an opening 96 is mounted to a tooth so that the marking point is accurately located in the center of the opening 96. Then the tooth is prepared, for example by etching, and the bracket is adhered to the tooth surface using a conventional method. The advantage of the arrangement of FIG. 12 is that the tooth may be prepared only at the portions desired, without having the preparation solution contact other portions of the teeth. Essentially, the tape of FIG. 12 acts as a mask in such an instance.

Figure 13:
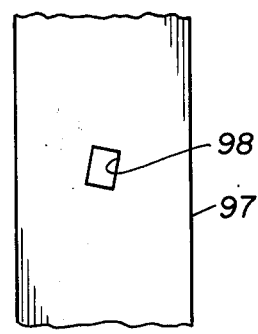
FIG. 13 illustrates a still further aspect of the invention.

FIG. 13 illustrates a tape 97 with an angularly oriented opening 98 therein. A bracket, or the like, is mounted to the angularly oriented opening 98 similarly to the embodiment shown in FIGS. 1 and 2. In FIG. 13, however, the angular orientation of the opening 98 is fixed. Different tapes are supplied with different openings located at different angular orientations.

While the apparatus and method have been described above with respect to specific embodiments, it should be clear that various modifications and alterations may be made to the invention without departing from the inventive concept as defined in the appended claims. While the particular tape described herein is preferred at this time, other tapes having the property of adhering to wet or damp surfaces may be used. Moreover, while tapes having at least some degree of elasticity are preferable, tapes without any elasticity may be used, as should be apparent. The tapes may have adhesive protected by a peel off backing, or may be provided in a roll without a backing, individual segments of tape being, for example, perforated so as to be easily removable from the roll. The above modifications are merely exemplary of the many modifications which are included within the inventive concept.

I claim:

1. Apparatus for mounting an orthodontic appliance on a tooth comprising: ;p1 an adhesive member which is adapted to be temporarily adhered to a surface of a tooth;
   said adhesive member including means for mounting an orthodontic appliance thereon in a given orientation relative to said adhesive member; and
   said adhesive member further including means for measuring and indicating an orientation of said orthodontic appliance relative to at least one of said adhesive member and a tooth.

2. Apparatus according to claim 1 wherein said measuring and indicating means comprises index markings on said adhesive member for measuring and indicating at least an angular orientation of an orthodontic appliance relative to said adhesive member.

3. Apparatus according to claim 2 wherein said measuring and indicating means further comprises index markings on said adhesive member for measuring and indicating the vertical orientation of said orthodontic appliance relative to a face of a tooth.

4. Apparatus according to claim 1 wherein said measuring and indicating means further comprises index markings on said adhesive member for measuring and indicating the vertical orientation of an orthodontic appliance relative to a face of a tooth.

5. Apparatus according to claim 1 wherein said mounting means comprises an opening in said adhesive member for receiving at least a portion of an orthodontic appliance therethrough.

6. Apparatus according to claim 5 wherein said orthodontic appliance is an orthodontic bracket.

7. Apparatus according to claim 6 wherein said opening has serrated edges for gripping said orthodontic bracket inserted through the opening.

8. Apparatus according to claim 5 wherein said opening is oval.

9. Apparatus according to claim 8 wherein said adhesive member is an elongated tape-like member and said oval has its longest dimension oriented substantially parallel to the longitudinal direction of said adhesive member.

10. Apparatus according to claim 1 wherein said orthodontic appliance is a twin orthodontic bracket having a space between the brackets thereof, and said measuring and indicating means of said adhesive member comprises angularly orienting means adapted to be received in said space between said brackets.

11. Apparatus according to claim 1 wherein said adhesive member is elongated and comprises first and second portions and a third portion interposed between said first and second portions, said third portion being oriented at an angle relative to the longitudinal direction of said mounting member.

12. Apparatus according to claim 1 wherein said adhesive member has an elongated slit along an end portion thereof in the direction of the length thereof.

13. Apparatus according to claim 1 wherein said adhesive member has adhesive on at least one flat surface thereof, and comprising a backing member removably covering said adhesive.

14. Apparatus according to claim 1 wherein said adhesive member has adhesive on both opposing flat surfaces thereof, and respective backing members removably mounted thereon and covering the respective adhesive surfaces.

15. Apparatus according to claim 13 wherein said adhesive adheres to a damp or wet surface.

16. Apparatus according to claim 5 further comprising encapsulation means covering at least a portion of the surface of said adhesive member in the vicinity of the opening thereof, said encapsulation means being carried by said adhesive member.

17. Apparatus according to claim 1 further comprising encapsulation means adapted to cover an orthodontic appliance mounted on said adhesive member, said encapsulation means being carried by said adhesive member.

18. Apparatus according to claim 1 wherein said adhesive member has a plurality of openings therein which are in registration with a plurality of respective teeth, each of said openings being adapted to receive an orthodontic appliance for mounting on respective teeth.

19. Apparatus according to claim 18 wherein said openings are arranged at predetermined angular orientations for mounting of said orthodontic appliances at predetermined angular orientations on said respective teeth.

20. Apparatus according to claim 1 wherein said measuring and indicating means of said adhesive member comprises an opening therein for removably receiving an orthodontic appliance, said opening being oriented at a predetermined angular orientation relative to said adhesive member for holding said orthodontic appliance at said predetermined angular orientation.

21. Method for positioning and mounting an orthodontic appliance on a tooth, comprising:
   removably mounting an orthodontic appliance on an adhesive member with a given orientation relative to the adhesive member, said adhesive member having means thereon for measuring and indicating the orientation of said appliance relative to at least one of said adhesive member and a tooth;
   adhering said adhesive member to a surface of a tooth with a given orientation relative to the tooth, and adhering said appliance to said surface of said tooth, said orthodontic appliance being thereby mounted to the tooth at a predetermined orientation to said tooth; and
   removing said adhesive member from said tooth and appliance after the adhesive securing appliance to said tooth has set.

22. Method according to claim 21 further comprising wrapping said adhesive member around the biting edge of the tooth and securing same to the inner surface of the tooth which is opposite from said outer surface, thereby improving retention of said adhesive member to said tooth.

23. Method according to claim 21 comprising adhering said adesive member to said tooth with an adhesive which adheres to a wet or damp surface.

24. Method for positioning and mounting an orthodontic appliance on a tooth, comprising:
adhering an adhesive member having at least one opening therein on a surface of at least one tooth with said at least one opening having a predetermined orientation relative to said at least one tooth, said adhesive member having means for measuring and indicating the orientation of said orthodontic appliance relative to at least one of said adhesive member and a tooth;
mounting an orthodontic appliance on said at least one tooth through said opening in said adhesive member at a given orientation relative to said at least one tooth; and
removing said adhesive member from said tooth after said appliance is mounted to said tooth.

25. Method according to claim 24 comprising adhering said adhesive member to a plurality of teeth, marking mounting points on said adhesive member in registration with each of said teeth, said mounting points corresponding to desired mounting points for orthodontic appliances, and forming openings in said adhesive member at said mounting points so as to expose portions of said teeth for mounting of said orthodontic appliances at said mounting points.

26. Method according to claim 25 comprising forming said openings with predetermined angular orientations on said adhesive member.

27. Method according to claim 25 comprising mounting orthodontic appliances in said openings such that said adhesive member retains said orthodontic appliances in position during mounting thereof on said teeth.

28. Method according to claim 23 comprising adhering said adhesive member to the gingival tissue.

29. Method according to claim 21 comprising removably mounting said adhesive member to a tooth only on at least one of the buccal-labial, lingual and incisal-occlusal surfaces of the tooth.

30. Method for positioning and mounting an orthodontic appliance on a tooth, comprising:
removably mounting an orthodontic appliance on an adhesive member with a given orientation relative to the adhesive member;
adhering said adhesive member to a tooth only on at least one of the buccal-labial, lingual and incisalocclusal surfaces of the tooth with a given orientation relative to the tooth, and adhering said appliance to said surface of said tooth, said orthodontic appliance being thereby mounted to the tooth at a predetermined orientation relative to said tooth; and
removing said adhesive member from said tooth and appliance after the adhesive securing said appliance to said tooth has set.

31. Method according to claim 30 comprising adhering said adhesive member to all of said surface of a tooth.

32. Method according to claim 30 comprising adhering said adhesive member to the gingival tissue.

33. Method for positioning and mounting an orthodontic appliance on a tooth, comprising:
adhering an adhesive member having at least one opening therein on at least one tooth only on at least one of the buccal-labial, lingual and incisalocclusal surfaces of said at least one tooth with said at least one opening having a predetermined location relative to said at least one tooth;
mounting an orthodontic appliance on said at least one tooth through said opening in said adhesive member at a given orientation relative to said at least one tooth; and then
removing said adhesive member from said tooth after said appliance is mounted to said tooth.

34. Method according to claim 33 comprising adhering said adhesive member to a plurality of teeth, marking mounting points on said adhesive member in registration with each of said teeth, said mounting points corresponding to desired mounting points for orthodontic appliances, and forming openings in said adhesive member at said mounting points so as to expose portions of said teeth for mounting of said orthodontic appliances at said mounting points.

35. Method according to claim 34 comprising forming said openings with predetermined angular orientations on said adhesive member.

* * * * *

UNITED STATES PATENT AND TRADEMARK OFFICE
CERTIFICATE OF CORRECTION

PATENT NO. : 4,117,596
DATED : October 3, 1978
INVENTOR(S) : Melvin WALLSHEIN

It is certified that error appears in the above-identified patent and that said Letters Patent are hereby corrected as shown below:

Column 7, line 22, after "comprising:" delete " ;p1" and begin a new paragraph with "an adhesive member...";

Column 8, line 61, before "to said tooth" insert --relative--.

Signed and Sealed this

Sixteenth Day of January 1979

[SEAL]

Attest:

RUTH C. MASON
Attesting Officer

DONALD W. BANNER
Commissioner of Patents and Trademarks